(12) United States Patent
Yu et al.

(10) Patent No.: US 9,213,017 B2
(45) Date of Patent: Dec. 15, 2015

(54) ROTARY ULTRASONIC TESTING APPARATUS WITH HYDRAULIC LIFTING UNITS

(71) Applicant: General Electric Company, Schenectady, NY (US)

(72) Inventors: Xun Yu, Shanghai (CN); Hua Zhou, Shanghai (CN); Kai Fan, Shanghai (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 468 days.

(21) Appl. No.: 13/658,841

(22) Filed: Oct. 24, 2012

(65) Prior Publication Data

US 2014/0109676 A1 Apr. 24, 2014

(51) Int. Cl.
| | |
|---|---|
| *G01H 1/12* | (2006.01) |
| *G01N 27/90* | (2006.01) |
| *G01N 29/22* | (2006.01) |
| *G01N 29/265* | (2006.01) |
| *G01N 29/28* | (2006.01) |

(52) U.S. Cl.
CPC .......... *G01N 27/9013* (2013.01); *G01N 29/225* (2013.01); *G01N 29/265* (2013.01); *G01N 29/28* (2013.01); *G01N 2291/2634* (2013.01)

(58) Field of Classification Search
CPC ..................................................... F16M 13/02
USPC ........................................................... 73/622
See application file for complete search history.

(56) References Cited

U.S. PATENT DOCUMENTS

| | | | |
|---|---|---|---|
| 3,077,768 A | 2/1963 | Allardt et al. | |
| 3,281,667 A | 10/1966 | Dobbins et al. | |
| 3,553,570 A | 1/1971 | Skubiak et al. | |
| 3,582,771 A * | 6/1971 | Placke | 324/226 |
| 3,689,829 A * | 9/1972 | Miller | 324/261 |
| 3,736,501 A * | 5/1973 | Donkin | G01N 27/9013 324/242 |
| 3,837,202 A | 9/1974 | Hetherington et al. | |
| 3,955,425 A * | 5/1976 | Corneau | B29C 47/92 73/622 |
| 4,246,794 A * | 1/1981 | Sheets | G01N 29/26 73/637 |
| 4,328,708 A * | 5/1982 | Bagwell | G01N 29/26 73/622 |
| 4,386,527 A * | 6/1983 | Maucher | G01N 29/07 73/597 |
| 4,718,277 A | 1/1988 | Glascock | |
| 4,760,737 A * | 8/1988 | Kupperman | G01N 29/11 73/622 |
| 5,313,837 A | 5/1994 | Haynes | |
| 7,757,559 B2 | 7/2010 | Venezel | |

FOREIGN PATENT DOCUMENTS

GB  2197070 A  5/1988

OTHER PUBLICATIONS

International Invitation to Pay Additional Fees dated Mar. 5, 2014 issued in connection with corresponding PCT Application No. PCT/US2013/066619.
International Search Report and Written Opinion issued in connection with corresponding PCT Application No. PCT/US2013/066619 dated Jun. 16, 2014.

* cited by examiner

*Primary Examiner* — Hezron E Williams
*Assistant Examiner* — Mark A Shabman
(74) *Attorney, Agent, or Firm* — Cooper Legal Group, LLC

(57) ABSTRACT

The present application provides a rotary testing apparatus for use with a work piece. The rotary testing apparatus may include a rotor, a probe, and a lifting unit for maneuvering the probe about the work piece. The lifting unit may include a hydraulic lifting mechanism and a counterweight mechanism.

6 Claims, 3 Drawing Sheets

ROTARY ULTRASONIC TESTING APPARATUS WITH HYDRAULIC LIFTING UNITS

TECHNICAL FIELD

The present disclosure relates generally to ultrasonic devices used for non-destructive testing and more particularly relates to a rotary ultrasonic testing apparatus with a number of hydraulic lifting units for testing of pipes, tubes, and the like in a fast and efficient manner.

BACKGROUND OF THE INVENTION

Non-destructive testing such as ultrasonic testing may be used to inspect various types of materials and components. Specifically, ultrasonic testing is a suitable method for finding internal flaws and/or certain material characteristics such as thickness and the like in many types of components made from sound conducting materials. Generally described, flaws or characteristics may be detected based upon changes in the reflection of sound waves on a boundary surface of the component. Such ultrasonic component testing is generally considered to provide highly accurate and repeatable results.

Ultrasonic testing of, for example, pipes, tubes, axels with bores, and the like may be performed by a rotary ultrasonic testing apparatus. Such an apparatus may have a number of ultrasonic probes positioned about a rotor. The apparatus may spiral along the length of the tube during an inspection. Because the ultrasonic probes need to stay in physical contact with the wall of the tube so as to provide accurate results, such rotary ultrasonic testing apparatuses may be somewhat heavy and slow in advancing along the length of the tube.

There is thus a desire for an improved rotary ultrasonic testing apparatus. Such an improved apparatus may provide adequate contact between the ultrasonic probes and the wall of the tube while advancing along the length of the tube in a fast and efficient manner.

SUMMARY OF THE INVENTION

The present application thus provides a rotary testing apparatus for use with a work piece. The rotary testing apparatus may include a rotor, a probe, and a lifting unit for maneuvering the probe about the work piece. The lifting unit may include a hydraulic lifting mechanism and a counterweight mechanism.

The present application further provides a lifting unit for a probe used in a rotary ultrasonic testing apparatus. The lifting unit may include a lifting unit base, a counterweight mechanism, a hydraulic lifting mechanism, and a gear wheel positioned between the counterweight mechanism and the hydraulic lifting mechanism for movement therewith.

The present application further provides a method of maneuvering a probe of a rotary testing apparatus about a work piece. The method may include the steps of moving a piston of a hydraulic cylinder in a first direction, moving a cam plate in the first direction by the piston of the hydraulic cylinder, moving a cam follower in a second direction by the cam plate, raising the probe off of the work piece by the cam follower, and lowering a counterweight by the cam follower.

These and other features and improvements of the present disclosure and the resultant patent will become apparent to one of ordinary skill in the art upon review of the following detailed description when taken in conjunction with the several drawings and the appended claims.

DETAILED DESCRIPTION

Figure 1:
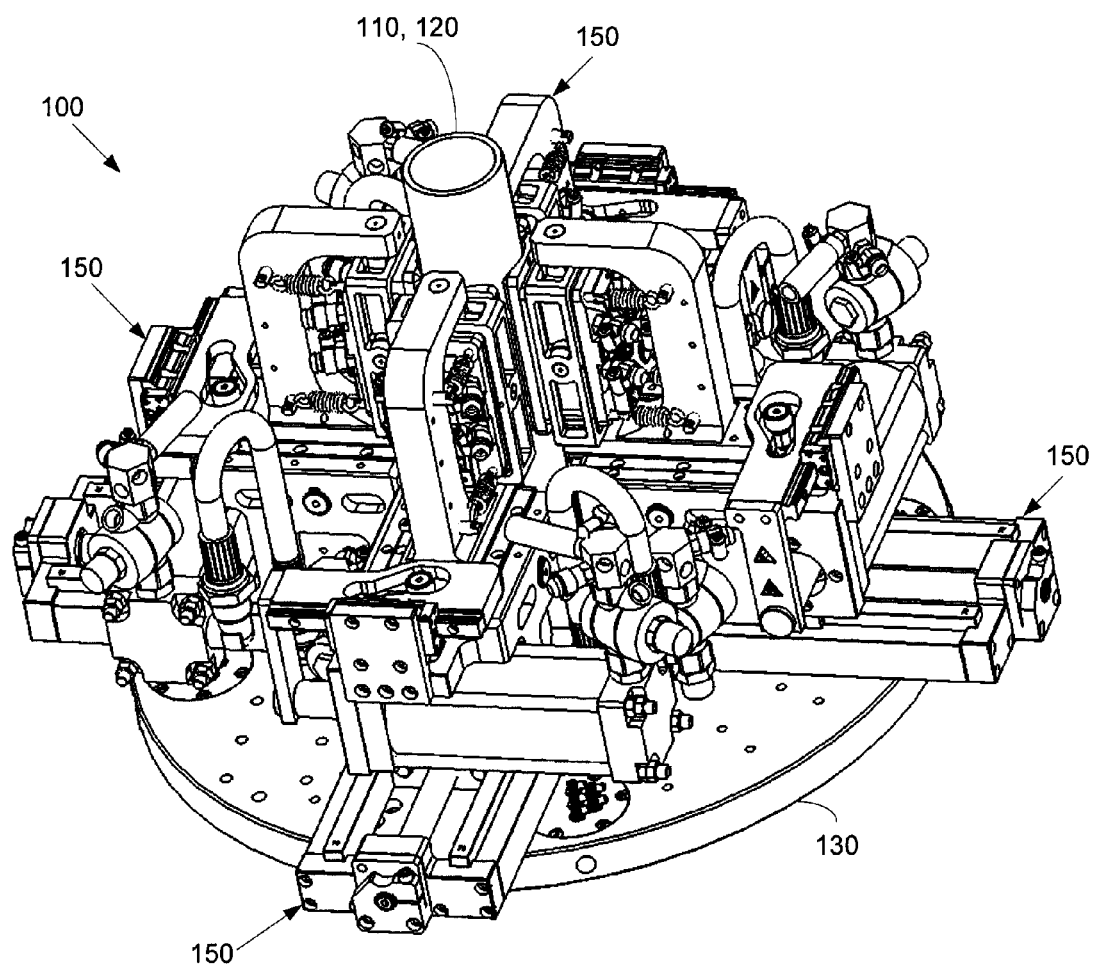
FIG. 1 is a perspective view of a rotary ultrasonic testing apparatus as may be described herein positioned about a tube.
Figure 2:
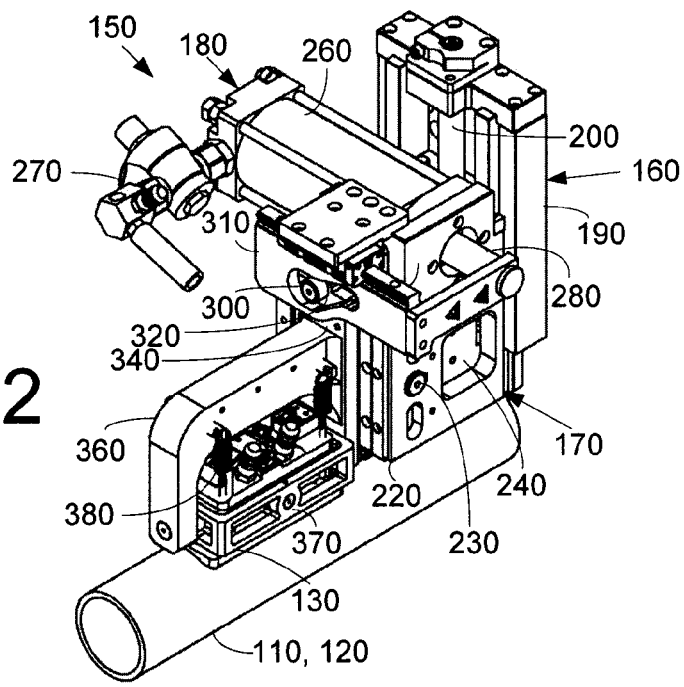
FIG. 2 is a perspective view of a lifting unit that may be used with the rotary ultrasonic testing apparatus of FIG. 1 positioned about the tube.
Figure 3:
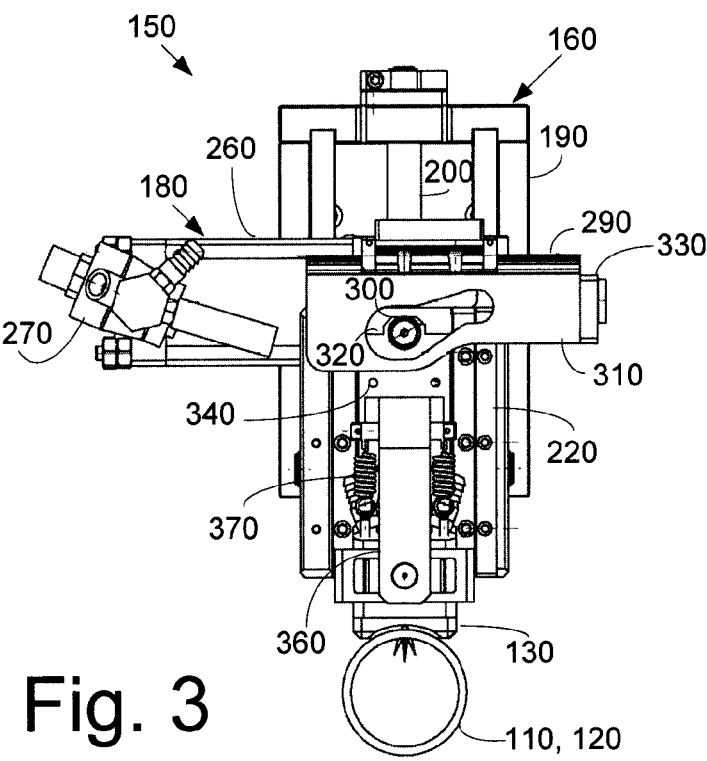
FIG. 3 is a front plan view of the lifting unit of FIG. 2 positioned about the tube.
Figure 4:
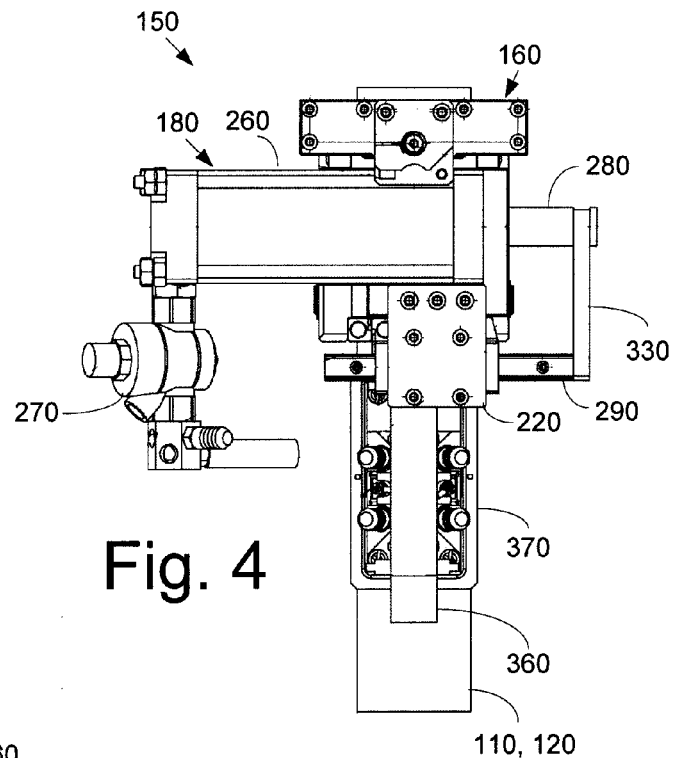
FIG. 4 is a top plan view of the lifting unit of FIG. 2 positioned about the tube.
Figure 5:
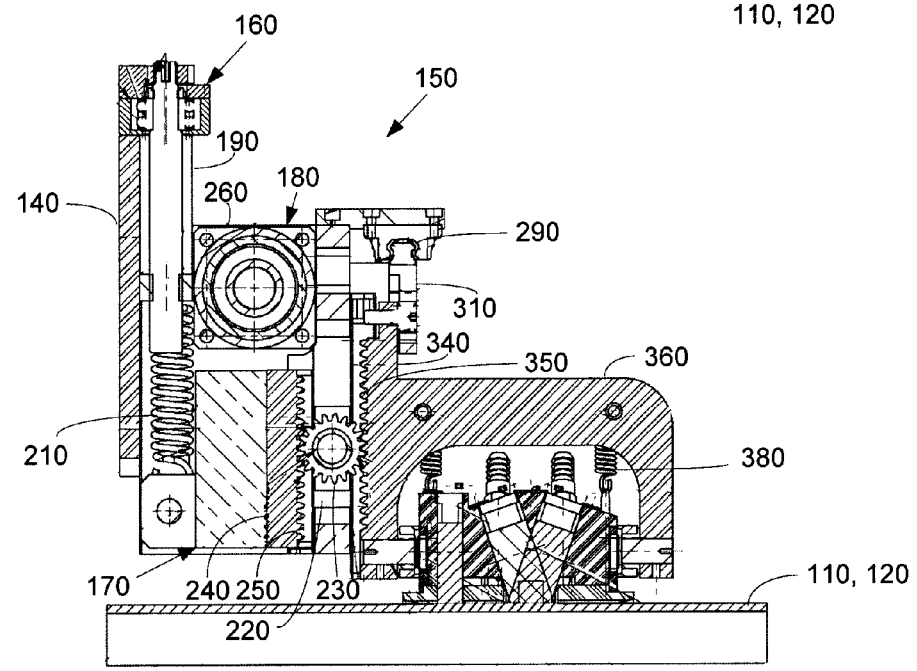
FIG. 5 is a side cross-sectional view of the lifting unit of FIG. 2 positioned about the tube.

Referring now to the drawings, in which like numerals refer to like elements throughout the several views, FIG. 1 shows a rotary ultrasonic testing apparatus 100 as may be described herein. The rotary ultrasonic testing apparatus 100 may be used with a work piece 110. In this example, the work piece 110 may be a tube 120. The tube 120 may be a length of pipe, an axel, or any type of substantially tubular structure and the like. The tube 120 may have any size, shape, or configuration. The rotary testing apparatus 100 may include a number of probes 130 positioned thereon. The probes 130 may be ultrasonic probes and the like. The probes 130 may be of conventional design. The probes 130 may be mounted on a rotor 140 via a number of lifting units 150. The rotary ultrasonic testing apparatus 100 also may include a drive mechanism (not shown) thereabout so as to spiral along the length of the tube 120 during an inspection. The data and/or images produced by the rotary ultrasonic testing apparatus 100 may be processed in a conventional manner. The rotary ultrasonic testing apparatus 100 and the components thereof may have any suitable size, shape, or configuration. Other components and other configurations may be used herein.

FIGS. 2-5 show an example of the lifting unit 150 of the rotary ultrasonic testing apparatus 100. The lifting unit 150 raises and lowers the probe 130 onto and off of the tube 120. The lifting unit also maintains the probe 130 in good physical contact with the tube 120 when lowered and in motion. Any number of lifting units 150 may be used herein. Generally described, the lifting unit 150 may include a lifting unit base 160, a counterweight mechanism 170, and a hydraulic lifting mechanism 180. Other components and other configurations may be used herein.

The lifting unit base 160 may be attached to the rotor 140 by conventional means. The lifting unit base 160 may include a pair of spring housings 190 and a counterweight rail 200. The spring housings 190 may have base extension springs 210 therein. Any number of the base extension springs 210 may be used herein in any suitable size, shape, or configuration. The base extension springs 210 may be in communication with the counterweight mechanism 170. The counterweight mechanism 170 may maneuver along the counterweight rail 200. Other types of guide mechanism may be used herein with the counterweight mechanism 170. Other components and other configurations may be used herein.

The counterweight mechanism 170 and the hydraulic lifting mechanism 180 may be positioned about a slider base 220. The slider base 220 may be attached to the lifting unit base 160 or otherwise fixably mounted. The slider base 220 may include a rotating gear wheel 230. The gear wheel 230 may be of conventional design and may have any suitable size, shape, or configuration. Other types of force transmission mechanisms may be used herein. Other components and other configurations may be used herein.

The counterweight mechanism 170 includes a counterweight 240. The counterweight 240 may have any suitable size, shape, or configuration. The counterweight 240 may be in communication with the base extension springs 210 on one end and an inner rack 250 on the other. The inner rack 250 cooperates with the gear wheel 230 in a rack and pinion configuration. The inner rack 250 may have any suitable size, shape, or configuration so as to cooperate with the gear wheel 230. Other components and other configurations may be used herein.

The hydraulic lifting mechanism 180 may include a hydraulic cylinder 260. The hydraulic cylinder 260 may be operated by water pressure although other types of working fluids may be used herein. The hydraulic cylinder 260 may be of conventional design and may be any suitable size, shape, or configuration. The hydraulic cylinder 260 may be attached to the lifting unit base 160 or otherwise fixably mounted. The hydraulic cylinder 260 may include a pressure relief valve 270. The hydraulic cylinder 260 may drive a piston 280 in reciprocal motion along a first direction with a spring return. The water pressure may be about eight (8) bar or so. Other pressures also may be used herein. The water pressure may drive the piston 280 so as to compress the internal spring. Releasing this pressure allows the internal spring to drive the return of the piston 280. The flow of water may be routed to the hydraulic cylinder 260 via the rotor 140. A portion of the flow of water may be used at a lower pressure to couple the probe 130 to the tube 120. Other components and other configurations also may be used herein.

The hydraulic lifting mechanism 180 also may include a slider bar 290 positioned for movement along the slider base 220 in the first direction. The slider bar 290 may be attached to and support a cam plate 310 for movement therewith. The cam plate 310 may include an internal cam guide 320. The cam plate 310 also may be in communication with the piston 280 of the hydraulic cylinder 260 via a piston flange 330 for movement therewith in the first direction. The slider bar 290 and the cam plate 310 may have any suitable size, shape, or configuration.

The hydraulic lifting mechanism 180 also may include a cam follower 340 in communication with and supported by the cam plate 310. The cam follower 340 may have a slider roller 300 positioned thereon. The slider roller 300 may be positioned within the internal cam guide 320 of the cam plate 310. Movement of the cam plate 310 in the first direction causes the slider roller 300 and the cam follower 340 to move in a second direction. The first direction and the second direction may be substantially perpendicular to each other. The slider roller 300 and the cam follower 340 may have any suitable size, shape, or configuration.

The cam follower 340 may include an outer rack 350. The outer rack 350 may cooperate with the gear wheel 230 in a rack and pinion configuration as described above. The outer rack 350 may have any suitable size, shape, or configuration to cooperate with the gear wheel 230. The cam follower 340 also includes an outer frame 360 extending from the outer rack 350. The outer frame 360 may support a probe shoe 370 therein. The probe 130 may be positioned within the probe shoe 370. The outer frame 360 and the probe shoe 370 may have any suitable size, shape, or configuration. A number of probe extension springs 380 also may connect the floating frame 360 and the probe 130. Any type of extension springs 380 may be used herein. Other components and other configurations may be used herein.

In use, the hydraulic lifting mechanism 180 of the lifting unit 150 lifts and lowers the probe 130 about the wall of the tube 120. Specifically, retracting the piston 280 of the hydraulic cylinder 260 causes the cam plate 310 to raise the cam follower 340 via the slider roller 300 and the internal cam guide 320 and, hence, to raise the probe 130 off of the tube 120. This upward movement of the cam follower 340 also drives the counterweight mechanism 170 downward via the interaction of the gear wheel 230, the inner rack 250, and the outer rack 350. This downward movement also extends the base extension springs 210.

Likewise, extending the piston 280 of the hydraulic cylinder 260 releases the slider roller 300 of the cam plate 310 from the internal cam guide 320 of the cam plate 310. Once this contact is released, the counterweight mechanism 170 and the base extension springs 210 extend upward and, hence, force the cam follower 340 downward via the interaction of the gear wheel 230, the inner rack 250, and the outer rack 350 such that the probe 130 contacts the tube 120.

This downward force also maintains the contact between the probe 130 and the tube 120. Specifically, the centrifugal force caused by the rotation of the overall rotary ultrasonic testing apparatus 100 generated by the counterweight 240 and the probe 130 generally may be equal. As such, the force generated by the base extension springs 210 may be the clamping force maintaining the probe 130 in contact with the tube 120. Other components and other configurations may be used herein.

The lifting units 150 of the rotary ultrasonic testing apparatus 100 thus accurately and efficiently position the probes 130 about the tube 120 or other type of structure. Moreover, the lifting units 150 are comparatively compact and light weight as compared to known units so as to allow the rotary ultrasonic testing apparatus 100 to travel at a higher overall rotational speed while maintaining adequate contact with the tube 120 during an inspection. The rotary ultrasonic testing apparatus 100 described herein thus provides ultrasonic testing of the tube 120 and the like in a high speed and efficient manner.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

We claim:

1. A lifting unit for a probe used in a rotary ultrasonic testing apparatus, comprising:
   a lifting unit base;
   a counterweight mechanism;
   a hydraulic lifting mechanism; and
   a gear wheel positioned between the counterweight mechanism and the hydraulic lifting mechanism;
   wherein the counterweight mechanism comprises a first rack, wherein the hydraulic lifting mechanism comprises a second rack, and wherein the gear wheel is positioned between the first rack and the second rack.

2. The lifting unit of claim 1, wherein the lifting unit base comprises a base extension spring attached to the counterweight mechanism.

3. The lifting unit of claim 1, wherein the hydraulic lifting mechanism comprises a hydraulic cylinder.

4. The lifting unit of claim 3, wherein the hydraulic lifting mechanism comprises a cam plate in communication with the hydraulic cylinder for motion in a first direction.

5. The lifting unit of claim 4, wherein the hydraulic lifting mechanism comprises a cam follower in communication with the cam plate for motion in a second direction.

6. The lifting unit of claim 5, wherein the hydraulic lifting mechanism comprises a probe shoe attached to the cam follower for maneuvering the probe.

* * * * *